(12) United States Patent
O'Connell et al.

(10) Patent No.: US 8,821,852 B2
(45) Date of Patent: Sep. 2, 2014

(54) VACCINES WITH LIVE BACTERIAL ISOLATES FOR SYSTEMIC ADMINISTRATION

(75) Inventors: Kevin A. O'Connell, Omaha, NE (US); Rhonda LaFleur, Omaha, NE (US); Huchappa Gowda Jayappa, Omaha, NE (US); Terri L. Wasmoen, Omaha, NE (US)

(73) Assignee: Intervet Inc., Summit, NJ (US)

( * ) Notice: Subject to any disclaimer, the term of this patent is extended or adjusted under 35 U.S.C. 154(b) by 0 days.

(21) Appl. No.: 13/995,740

(22) PCT Filed: Dec. 21, 2011

(86) PCT No.: PCT/IB2011/003100
§ 371 (c)(1),
(2), (4) Date: Jun. 19, 2013

(87) PCT Pub. No.: WO2012/085642
PCT Pub. Date: Jun. 28, 2012

(65) Prior Publication Data
US 2013/0273100 A1    Oct. 17, 2013

Related U.S. Application Data

(60) Provisional application No. 61/556,975, filed on Nov. 8, 2011, provisional application No. 61/425,855, filed on Dec. 22, 2010.

(30) Foreign Application Priority Data

Feb. 1, 2011   (EP) ..................... 11152829

(51) Int. Cl.
| | | |
|---|---|---|
| *A01N 63/00* | (2006.01) | |
| *A01N 65/00* | (2009.01) | |
| *A61K 39/12* | (2006.01) | |
| *A61K 39/02* | (2006.01) | |
| *A61K 39/00* | (2006.01) | |

(52) U.S. Cl.
CPC ........... *A61K 39/099* (2013.01); *A61K 2039/70* (2013.01); *A61K 2039/552* (2013.01); *A61K 2039/5252* (2013.01); *A61K 39/12* (2013.01); *A61K 2039/5254* (2013.01); *A61K 2039/55505* (2013.01); *C12N 2760/16134* (2013.01); *C12N 2760/18734* (2013.01); *A61K 2039/521* (2013.01); *A61K 2039/522* (2013.01)
USPC .................. 424/93.1; 424/93.2; 424/93.4

(58) Field of Classification Search
None
See application file for complete search history.

(56) References Cited

U.S. PATENT DOCUMENTS

| | | | |
|---|---|---|---|
| 5,840,556 A | 11/1998 | Briggs et al. | |
| 5,955,089 A * | 9/1999 | Briles et al. | ................. 424/244.1 |
| 7,959,929 B2 | 6/2011 | Crawford et al. | |
| 2005/0238657 A1 * | 10/2005 | Cornford-Nairn et al. | 424/200.1 |
| 2007/0082012 A1 * | 4/2007 | Shields et al. | ............. 424/209.1 |
| 2008/0254062 A1 | 10/2008 | Harvill | |
| 2009/0246222 A1 | 10/2009 | Locht et al. | |

FOREIGN PATENT DOCUMENTS

| | | |
|---|---|---|
| KR | 20080082883 A | 9/2008 |
| WO | 2010/125084 A1 | 11/2010 |

OTHER PUBLICATIONS

Plotkin (Vaccines W. B. Saunders Company, 1988, p. 571).*
Briggs et al., "Generation and Molecular Characterization of New Temperature-Sensitive Plasmids Intended for Genetic Engineering of Pasteurellaceae", Applied and Enviromental Microbiology, 2005, pp. 7187-7195, vol. 71(11).
Chladek et al., "Canine Parainfluenza-Bordetella Bronchiseptica Vaccine: Immunogenicity", American Journal of Veterinary Research, 1981, pp. 266-270, vol. 42(2).
Cox et al., "2,3-Dihydroxybenzoic Acid, a New Growth Factor for Multiple Aromatic Auxotrophs", Journal of Bacteriology, 1967, pp. 502-503, vol. 93(1).
Dougan et al., "Isolation of stable aroA mutants of *Salmonella typhi* Ty2: Properties and preliminary characterisation in mice", Molecular and General Genetics, 1987, pp. 402-405, vol. 207.
Ivins et al., "Immunization against Anthrax with Aromatic Compound-Dependent (Aro-) Mutants of *Bacillus anthracis* and with Recombinant Strains of *Bacillus subtilis* That Produce Anthrax Protective Antigen", Infection and Immunity, 1990, pp. 303-308, vol. 58(2).
Kim et al., "*Bordetella bronchiseptica* aroA mutant as a live vaccine vehicle for heterologous porcine circovirus type 2 major capsid protein expression", Veterinary Microbiology, 2009, pp. 318-324, vol. 138.
Marrack et al., "Towards an understanding of the adjuvant action of aluminium", Nature Reviews Immunology, 2009, pp. 287-293, vol. 9.
Moat et al., "Biosynthesis and Metabolism of Amino Acids", Microbial Physiology, 2002, Wiley-Liss, Chapter 15, pp. 525-527.
Musser et al., "Clonal Diversity and Host Distribution in *Bordetella bronchiseptica*", Journal of Bacteriology, 1987, pp. 2793-2803, vol. 169(6).
Roberts et al., "Construction and Characterization in Vivo of *Bordetella pertussis* aroA Mutants", Infection and Immunity, 1990, pp. 732-739, vol. 58(3).
Saiki et al., "Primer-Directed Enzymatic Amplification of DNA with a Thermostable DNA Polymerase", Science, 1988, pp. 487-491, vol. 239.
Stevenson et al., "Use of a rationally attenuated *Bordetella bronchiseptica* as a live mucosal vaccine vector for heterologous antigens", Vaccine, 2002, pp. 2325-2335, vol. 20.
Stevenson et al., "Use of *Bordetella bronchiseptica* and *Bordetella pertussis* as live vaccines and vectors for heterologous antigens", FEMS Immunology and Medical Microbiology, 2003, pp. 121-128, vol. 37.
Stevenson et al., "Intranasal immunisation against tetanus with an attenuated *Bordetella bronchiseptica* vector expressing FrgC: improved immunogenicity using a Bvg-regulated rpomoter to express FrgC", Vaccine, 2004, pp. 4300-4305, vol. 22.

(Continued)

*Primary Examiner* — Albert Navarro

(57) ABSTRACT

The present invention pertains to vaccines suitable for administering systemically that comprise live aro mutant bacteria, an adjuvant, an aromatic supplement, or both an adjuvant and an aromatic supplement. The present invention also pertains to the manufacture of such a vaccine and a method of protecting an animal by administration of the vaccine.

23 Claims, No Drawings

(56) References Cited

OTHER PUBLICATIONS

Tatum et al., "Construction of In-Frame aroA Deletion Mutants of *Mannheimia haemolytica, Pasteurella multocida*, and *Haemophilus somnus* by Using a New Temperature-Sensitive Plasmid", Applied and Environmental Microbiology, 2005, pp. 7196-7202, vol. 71(11).

Toschach et al., "Hepatocellular Necrosis Associated with the Subcutaneous Injection of an Intranasal *Bordetella bronchiseptica*-Canine Parainfluenza Vaccine", Journal of the American Animal Hospital Association, 1997, pp. 126-128, vol. 33.

International Search Report for corresponding PCT/IB2011/003100, mailed on May 25, 2012.

Kim, et al., "Vaccine Potential of an attenuated *Pasteurella multocida* that expresses only the N-terminal truncated fragment of *P. multocida* toxin in pigs", The Canadian Journal of Veterinary Research, 2012, pp. 69-71, vol. 76.

* cited by examiner

VACCINES WITH LIVE BACTERIAL ISOLATES FOR SYSTEMIC ADMINISTRATION

CROSS-REFERENCE TO RELATED APPLICATIONS

This application is a national stage entry under 35 U.S.C. §371 of PCT/IB2011/003100, filed on Dec. 21, 2011, which claims priority to US Provisional Application Nos. 61/425,855, filed on December 2010; 61/556,975, filed on Nov. 8, 2011; and EP Application No. 11152829.5, filed on Feb. 1, 2011. The content of PCT/IB2011/003100 is hereby incorporated by reference in its entirety.

FIELD OF THE INVENTION

The present invention pertains to vaccines for systemic administration that comprise a live attenuated bacterial isolate. The invention also pertains to the manufacture of such vaccines and methods of vaccinating animal subjects.

BACKGROUND

*Bordetella bronchiseptica* (*B. bronchiseptica*) is a highly infectious Gram-negative bacterium that can efficiently colonize healthy ciliated respiratory mucosa to cause respiratory infections in a wide range of host species. Accordingly, *B. bronchiseptica* is an etiologic agent in both atrophic rhinitis in pigs and kennel cough in dogs.

Notably however, humans are far more likely to be infected by the better known *Bordetella pertussis* (*B. pertussis*) for which humans are the only natural target [see, Stevenson and Roberts, *FEMS Immunology and Medical Microbiology* 37:121-128 (2003)]. In addition, unlike *B. pertussis*, *B. bronchiseptica* does not express the pertussis toxin. Furthermore, whereas *B. pertussis* infections are not known to result in prolonged colonization in the upper respiratory tract, *B. bronchiseptica* causes chronic infection in the upper respiratory tract in a number of different animal species. Consistently, whereas the systemic administration of a live *B. pertussis* vaccine recently has been proposed for human subjects [see, U.S. Publication No. 2009/0246222 A1], heretofore, live attenuated *B. bronchiseptica* vaccines have been designed for local intra-nasal administration into non-human animals, e.g., Nobivac®KC and Intra-Trac II (available from Merck Animal Health), Recombitek® KC2 (available from Merial) and Bronchi-Shield III (available from Fort Dodge).

One particular way to generate a live attenuated bacterium is to modify one or more key genes of that bacterium. In many microorganisms chorismate is a critical intermediate in the biosynthesis of important aromatic compounds, including folic acid and the three aromatic amino acids, phenylalanine, tyrosine, and tryptophan [Moat et al., *Microbial Physiology* (2002) Wiley-Liss, Chapter 15, pgs. 525-527]. Therefore, inactivation of a gene within the biosynthetic pathway of chorismate, such as aroA, has been used to generate live attenuated bacteria. Accordingly, a significant number of bacteria have been constructed to contain a deletion in their aroA genes including: *Mannheimia haemolytica, Pasteurella multocida, Hemophilus somnus* [see, e.g., Briggs, and Tatum, *Applied and Environmental Microbiology,* 71(11) 7187-7195 (2005); Tatum and Briggs, *Applied and Environmental Microbiology,* 71 (11) 7196-7202. (2005); U.S. Pat. No. 5,840,556]; *Salmonella typhimurium* [Dougan et al., *Molecular and General Genetics,* 207(2-3) 402-405 (1987), and *B. pertussis* [Roberts et al., *Infectious Immunology* 58:732-739 (1990)]. However, heretofore, vaccines containing such aroA mutant bacteria have, for the most part, shown minimal if any success, see e.g., paragraph [0133] of U.S. Publication No. 2009/0246222 A1, which specifically refers to the rather limited success of vaccines comprising *B. pertussis* with an aroA deletion, and which strongly recommends instead the use of avirulent, live *B. pertussis* constructs with a mutation within a gene encoding one of the three major toxins of *B. pertussis*.

An aroA deletant strain of *B. bronchiseptica* also has been constructed [Stevenson and Roberts, Vaccine 20, 2325-2335 (2002)]. These workers employed their deletant aroA *B. bronchiseptica* strain solely in an intranasal vaccine. Intranasal vaccines however, are inconvenient to administer, especially to adult animals, such as canines or felines that often resist administration of any substance into their nostrils. Administering such intranasal vaccines also creates a risk that the amount of vaccine taken in by the animal will be significantly less than the dose shown to be protective, should the animal sneeze during the administration. On the other hand, heretofore, systemic administration of live vaccines has not been regarded as a safe option, since it is known that the systemic administration of live *B. bronchiseptica*, even when attenuated, can lead to serious abscess formation [see e.g., Toshach et al., *J Am Anim Hosp Assoc* 33:126-128 (1997)].

Several killed whole cell and sub-unit *B. bronchiseptica* vaccines also have been described for parenteral administration to dogs, including the killed whole cell *B. bronchiseptica* vaccine Bronchicine® CAe, which is available from Pfizer Animal Health. Unfortunately, there also are several disadvantages to such killed *B. bronchiseptica* vaccines. For example, lipopolysaccharides (LPS) are inherent to Gram-negative bacteria and therefore, systemic administration of a killed *B. bronchiseptica* vaccine may lead to endotoxic shock due to LPS. Accordingly, killed vaccines need to be highly purified to minimize the amount of LPS. Such purification makes the manufacture of the vaccine more complex, often leading to the loss of effective antigens, and thereby increasing the overall cost of production. Therefore, there remains a need to obtain a vaccine for systemic administration that is safe and efficacious against *B. bronchiseptica*.

The citation of any reference herein should not be construed as an admission that such reference is available as "prior art" to the instant application.

SUMMARY OF THE INVENTION

In order to overcome the deficiencies of current vaccines exemplified above, the present invention provides novel vaccines against bacterial infections, as well as their corresponding immunogenic compositions. The present invention also provides methods of administering such vaccines to an animal. The present invention further provides methods of preventing a disease in an animal through administering a vaccine of the present invention. In particular embodiments, the animal is a canine. In other embodiments, the animal is a feline. In still other embodiments, the animal is a porcine.

In particular embodiments, the vaccine comprises a live aro mutant bacterium that is in a form suitable for systemic administration. In certain embodiments, the live aro mutant bacterium is a live aroA mutant bacterium. In particular embodiments, the bacterium is *B. bronchiseptica*. In certain embodiments of this type, the vaccine comprises a live aroA mutant *B. bronchiseptica* strain. In particular embodiments of the present invention, a vaccine can aid in the protection of an animal and/or protect that animal against a disorder and/or clinical disease arising from an infection with *B. bronchiseptica*.

Vaccines of the present invention can comprise a live aro mutant bacterium and an aromatic supplement. In particular embodiments, the aromatic supplement of a vaccine of the present invention comprises tyrosine. In certain embodiments, the aromatic supplement of a vaccine of the present invention comprises tryptophan. In particular embodiments, the aromatic supplement of a vaccine of the present invention comprises phenylalanine. In certain embodiments, the aromatic supplement of a vaccine of the present invention comprises para-aminobenzoic acid. In particular embodiments, the aromatic supplement of a vaccine of the present invention comprises 2,3-dihydroxybenzoic acid. In certain embodiments, the aromatic supplement of a vaccine of the present invention comprises folic acid. In particular embodiments, the aromatic supplement of a vaccine of the present invention comprises enterobactin.

In particular embodiments, the aromatic supplement of a vaccine of the present invention comprises multiple aromatic compounds. Embodiments of any combination of two or more of such aromatic compounds can be comprised by an aromatic supplement of a vaccine of the present invention. In certain embodiments, the aromatic supplement of a vaccine of the present invention comprises phenylalanine and tryptophan. In particular embodiments, the aromatic supplement of a vaccine of the present invention comprises phenylalanine and tyrosine. In certain embodiments, the aromatic supplement of a vaccine of the present invention comprises tyrosine and tryptophan. In particular embodiments, the aromatic supplement of a vaccine of the present invention comprises phenylalanine, tyrosine, and tryptophan.

In particular embodiments, the aromatic supplement of a vaccine of the present invention comprises para-aminobenzoic acid and 2,3-dihydroxybenzoic acid. In certain embodiments, the aromatic supplement of a vaccine of the present invention comprises 2,3-dihydroxybenzoic acid and folic acid. In particular embodiments, the aromatic supplement of a vaccine of the present invention comprises folic acid and enterobactin. In certain embodiments, the aromatic supplement of a vaccine of the present invention comprises para-aminobenzoic acid and enterobactin.

In particular embodiments, the aromatic supplement of a vaccine of the present invention comprises phenylalanine, tyrosine, tryptophan, and para-aminobenzoic acid. In certain embodiments, the aromatic supplement of a vaccine of the present invention comprises phenylalanine, tyrosine, tryptophan, and folic acid. In particular embodiments, the aromatic supplement of a vaccine of the present invention comprises phenylalanine, tyrosine, tryptophan, and 2,3-dihydroxybenzoic acid. In certain embodiments, the aromatic supplement of a vaccine of the present invention comprises phenylalanine, tyrosine, tryptophan, and enterobactin. In particular embodiments, the aromatic supplement of a vaccine of the present invention comprises phenylalanine, tyrosine, tryptophan, para-aminobenzoic acid, and 2,3-dihydroxybenzoic acid.

In certain embodiments, a vaccine of the present invention comprises an adjuvant. In particular embodiments of this type, the adjuvant is an aluminum salt. In certain embodiments, the aluminum salt is aluminum phosphate. In other embodiments, the aluminum salt is aluminum hydroxide. In still other embodiments, the aluminum salt is aluminum potassium sulfate. In particular embodiments, a vaccine of the present invention comprises both an aromatic supplement and an adjuvant. In specific embodiments, the aromatic supplement of a vaccine of the present invention comprises phenylalanine, tyrosine, tryptophan, and para-aminobenzoic acid, and the adjuvant is aluminum hydroxide. In a particular embodiment of this type, the aromatic supplement of a vaccine of the present invention comprises phenylalanine, tyrosine, tryptophan, para-aminobenzoic acid, and 2,3-dihydroxybenzoic acid, and the adjuvant is aluminum hydroxide.

The present invention also provides multivalent vaccines. As is true of all vaccines of the present invention, the multivalent vaccines of the present invention can comprise an aromatic supplement and/or an adjuvant. In certain embodiments, the vaccine comprises a live aroA mutant *B. bronchiseptica* and a canine parainfluenza virus (CPI) antigen. In particular embodiments, the canine parainfluenza virus antigen is a modified live parainfluenza virus. In certain embodiments, the vaccine comprises a live aroA mutant *B. bronchiseptica* and a canine influenza virus (CIV) antigen. In particular embodiments, the canine influenza virus antigen is a killed canine influenza virus. In certain embodiments, the vaccine comprises a live aroA mutant *B. bronchiseptica* and both a canine influenza virus antigen and a canine parainfluenza virus antigen. In specific embodiments of this type, the canine influenza virus antigen is a killed canine influenza virus and the canine parainfluenza virus antigen is a modified live parainfluenza virus.

Specific multivalent vaccines of the present invention can comprise a live *B. bronchiseptica* aroA mutant that comprises a heterologous nucleic acid that encodes a foreign antigen (e.g., an antigen from another pathogen). The heterologous nucleic acid is operably linked to a promoter, thereby allowing the *B. bronchiseptica* aroA mutant to express that foreign antigen. In certain embodiments of this type, the heterologous nucleic acid encodes a viral antigen. In particular embodiments of this type, the viral antigen is an influenza virus antigen. In related embodiments, the influenza virus antigen is from a canine influenza virus. In other embodiments, the influenza virus antigen is from a feline influenza virus. In still other embodiments, the influenza virus antigen is from a porcine influenza virus. In certain embodiments, the influenza virus antigen is a hemagglutinin. In other embodiments, the influenza virus antigen is a neuraminidase.

In more specific embodiments, the viral antigen is a canine influenza virus H3 hemagglutinin. In other embodiments, the heterologous nucleic acid encodes an antigenic fragment of a canine influenza virus H3 hemagglutinin. In still other embodiments, the heterologous nucleic acid encodes a canine influenza virus N8 neuraminidase. In yet other embodiments, the heterologous nucleic acid encodes a canine influenza virus N2 neuraminidase. In still other embodiments, the *B. bronchiseptica* aroA mutant comprises multiple heterologous nucleic acids. In a particular embodiment of this type the *B. bronchiseptica* aroA mutant comprises both a heterologous nucleic acid encoding a canine influenza virus H3 hemagglutinin and a heterologous nucleic acid encoding a canine influenza virus N8 neuraminidase. In still other embodiments of this type the heterologous nucleic acid encodes both a H3 hemagglutinin and an N2 neuraminidase of the canine influenza virus.

In more specific embodiments, such multivalent vaccines further comprise an aromatic supplement and/or an aluminum salt adjuvant. In one such embodiment, the multivalent vaccine comprises an aromatic supplement and/or an aluminum salt adjuvant, and a live *B. bronchiseptica* aroA mutant comprising a canine influenza virus H3 hemagglutinin that is operably linked to a promoter. In certain embodiments, such multivalent vaccines further comprise a modified live parainfluenza virus.

All of the vaccines of the present invention can be lyophilized and/or have a lyophilized portion thereof (e.g., a fraction). In particular embodiments, the lyophilized vaccine or portion thereof is in the form of a freeze-dried cake. In related embodiments, the lyophilized vaccine or portion thereof is in the form of a freeze-dried sphere. In still other embodiments, the lyophilized vaccine or portion thereof is in the form of a freeze-dried oval and/or ellipsoid.

Accordingly, vaccines of the present invention can come in two or more different portions (e.g., fractions) with at least one being a freeze-dried fraction. In a related embodiment of this type, at least one other portion is a liquid. In a certain embodiments of this type, at least one portion is freeze-dried and at least one other is a liquid diluent. In particular embodiments a lyophilized portion of a multivalent vaccine of the present invention comprises one or more antigens, while the diluent comprises one or more different antigens. In more particular embodiments of this type, the lyophilized portion of a multivalent vaccine comprises a live aroA mutant *B. bronchiseptica*. In specific embodiments of this type, the lyophilized portion of a multivalent vaccine comprises a live aroA mutant *B. bronchiseptica* along with a modified live canine parainfluenza virus.

In related embodiments, the diluent comprises a killed canine influenza virus. In particular embodiments the diluent comprises an aromatic supplement and/or an adjuvant. In certain embodiments the lyophilized portion of a multivalent vaccine further comprises an aromatic supplement and/or an adjuvant. In particular embodiments both the lyophilized portion of a multivalent vaccine and the diluent comprise an aromatic supplement and/or an adjuvant. In specific embodiments, the lyophilized portion of a multivalent vaccine comprises a live aroA mutant *B. bronchiseptica* and a canine parinfluenza virus together with an aromatic supplement, while the diluent comprises a killed canine influenza virus and an adjuvant. In more specific embodiments, the adjuvant is 2 to 5% aluminum hydroxide.

The present invention further provides methods of aiding in the protection of an animal (including a human) against a clinical disease that arises from an infection with *B. bronchiseptica*. In particular embodiments, the method comprises administering a vaccine of the present invention systemically to an animal. In certain embodiments of this type, the animal is a mammal. In particular embodiments, the mammal is a pig. In other embodiments, the mammal is a canine. In still other embodiments, the mammal is a feline. In certain embodiments, administering a vaccine of the present invention systemically is performed by subcutaneous vaccination.

The present invention also provides the use of a live aro mutant *B. bronchiseptica* to manufacture a vaccine to protect an animal against a clinical disease arising from an infection with *B. bronchiseptica*. Preferably, the vaccine is in a form suitable for systemic administration. In certain embodiments of this type, the vaccine further comprises an adjuvant. In particular embodiments, the adjuvant is an aluminum salt. In more particular embodiments, the aluminum salt is aluminum hydroxide. In more other embodiments, the aluminum salt is aluminum phosphate. In other embodiments, the aluminum salt is aluminum potassium sulfate.

In certain embodiments, the vaccine further comprises an aromatic supplement. In particular embodiments, the vaccine comprises both an adjuvant and an aromatic supplement. In more specific embodiments, the adjuvant is aluminum hydroxide, and the aromatic supplement comprises phenylalanine, tyrosine, tryptophan, para-aminobenzoic acid, and 2,3-dihydroxybenzoic acid.

These and other aspects of the present invention will be better appreciated by reference to the following Detailed Description.

DETAILED DESCRIPTION OF THE INVENTION

In contrast to killed antigens, the live aro mutant bacteria of the present invention are attenuated. Consequently, care must be taken when formulating a vaccine to maintain the titer of the attenuated bacterium at a level that is safely below that which can lead to a significant adverse event. However, achieving such a safe level often leads to a substantial decline in the efficacy of the live attenuated vaccine. The present invention has overcome this problem by augmenting the efficacy of the vaccine without increasing the titer of the live attenuated bacterial antigen added to the vaccine. In addition, the present invention provides a means for lowering the cost of manufacture of the vaccines provided by significantly reducing the amount of live attenuated bacteria necessary to make a safe and efficacious vaccine.

Accordingly, the present invention provides safe and efficacious vaccines that comprise a live aro mutant bacterium in a form suitable for systemic administration. In one aspect, the present invention provides a vaccine comprising a live aro mutant bacterium and an aromatic supplement. In particular embodiments, the live aro mutant bacterium is an aroA mutant bacterium. Surprisingly, the efficacy of a vaccine comprising a live aroA mutant bacterium was found to significantly increase when an aromatic supplement was added to that vaccine composition, without causing unacceptable injection site reactions.

In another aspect, the present invention provides live attenuated vaccines that show greater efficacy due to the presence of an adjuvant. Often, such improvement of efficacy achieved by adding an adjuvant severely amplifies negative side effects. Therefore, it was unexpectedly found that the efficacy of a vaccine comprising an aro mutant of *Bordetella bronchiseptica* could be improved by the addition of an adjuvant, while still retaining its safety at an acceptable level. This result leads to, inter alia, an increase in the range of effective doses for such vaccines.

In still another aspect, the present invention provides live attenuated aro mutant bacterial vaccines that show greater efficacy due to the presence of both an adjuvant and an aromatic supplement, while still retaining the safety of the vaccine at an acceptable level.

The present invention further provides methods of using a live *B. bronchiseptica* aro mutant to manufacture a vaccine for systemic administration, in order to protect an animal against a clinical disease arising from an infection with *B. bronchiseptica*. The present invention also pertains to a method to protect an animal against a clinical disease arising from *B. bronchiseptica* infection, which comprises the systemic administration of a vaccine comprising a live aro mutant *B. bronchiseptica* strain.

As used herein the following terms shall have the definitions set out below:

As used herein, a "vaccine" is a composition that is suitable for application to an animal (including, in certain embodiments, humans) comprising one or more antigens typically combined with a pharmaceutically acceptable carrier such as a liquid containing water, which upon administration to the animal induces an immune response strong enough to minimally aid in the protection from a clinical disease arising from an infection with a wild-type micro-organism, i.e., strong enough for aiding in the prevention of the clinical disease, and/or preventing, ameliorating, or curing the clinical disease.

As used herein, a "multivalent vaccine" is a vaccine that comprises two or more different antigens. In a particular embodiment of this type, the multivalent vaccine stimulates the immune system of the recipient against two or more different pathogens.

As used herein, the terms "protecting" or "providing protection to" and "aids in the protection" do not require complete protection from any indication of infection. For example, "aids in the protection" can mean that the protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

As used herein, the term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient.

The term "carrier" refers to a diluent, adjuvant, excipient, or vehicle with which the compound is administered. Pharmaceutical acceptable carriers can be sterile liquids, such as water and/or oils, including those of petroleum, animal, vegetable or synthetic origin, such as peanut oil, soybean oil, mineral oil, sesame oil and the like. Water or aqueous solution saline solutions and aqueous dextrose and glycerol solutions can be employed as carriers, particularly for injectable solutions.

As used herein, an "adjuvant" is a substance that is able to favor or amplify the cascade of immunological events, ultimately leading to a better immunological response, i.e., the integrated bodily response to an antigen. An adjuvant is in general not required for the immunological response to occur, but favors or amplifies this response.

As used herein, "systemic administration" is administration into the circulatory system of the body (comprising the cardiovascular and lymphatic system), thus affecting the body as a whole rather than a specific locus such as the gastro-intestinal tract (via e.g., oral or rectal administration) and the respiratory system (via e.g., intranasal administration). Systemic administration can be performed e.g., by administering into muscle tissue (intramuscular), into the dermis (intradermal, transdermal, or supradermal), underneath the skin (subcutaneous), underneath the mucosa (submucosal), in the veins (intravenous) etc.

"Parenteral administration" includes subcutaneous injections, submucosal injections, intravenous injections, intramuscular injections, intradermal injections, and infusion.

As used herein, the term "canine" includes all domestic dogs, *Canis lupus familiaris* or *Canis familiaris*, unless otherwise indicated.

As used herein, the term "feline" refers to any member of the Felidae family. Members of this family include wild, zoo, and domestic members, such as any member of the subfamilies Felinae, e.g., cats, lions, tigers, pumas, jaguars, leopards, snow leopards, panthers, North American mountain lions, cheetahs, lynx, bobcats, caracals or any cross breeds thereof.

Cats also include domestic cats, pure-bred and/or mongrel companion cats, show cats, laboratory cats, cloned cats, and wild or feral cats.

As used herein a "genetic alteration" of a gene in a bacterium may be due to a mutation and/or deletion and/or insertion into the gene and can include genetic events that occur naturally, and/or in a laboratory setting and by design e.g., through cell passaging, and/or through one or more recombinant genetic methods.

As used herein, an "aro mutant" bacterium is a bacterium that either cannot synthesize chorismate, or synthesizes significantly less chorismate than a corresponding wild-type bacterium, which consequently leads to a significant inhibition and/or blockage of the growth of the bacterium in an unsupplemented media, environment, or milieu. An aroA mutant bacterium can result from a genetic alteration of a gene within the chorismate biosynthetic pathway and/or a post-translational malfunction that leads to the comparable inhibition and/or inactivation of its corresponding gene product (i.e., the enzyme encoded by that gene).

As used herein, an "aroA mutant" bacterium is an aro mutant bacterium in which the genetic alteration is in the aroA gene and/or due to a post-translational malfunction that leads to a similar inhibition and/or inactivation of the corresponding aroA gene product.

As used herein, an "aromatic supplement" is a composition that comprises one or more aromatic compounds that can compensate, at least in part, for the inefficient growth of an aro mutant bacterium (e.g., an aroA mutant). Accordingly, the presence of an aromatic supplement in the media, environment, and/or milieu allows an aro mutant bacterium to grow more efficiently. Thus, an aromatic supplement can comprise one or more end-products of a biosynthetic pathway in which chorismate is an intermediate (e.g., an aromatic amino acid such as phenylalanine) and/or an intermediate that would otherwise be biosynthesized subsequent to chorismate in a biosynthetic pathway that includes chorismate (e.g., para-amino benzoic acid, which is an intermediate in the biosynthetic pathway of folic acid). An aromatic supplement also can comprise an alternative source for chorismate and/or an alternative source for one or more intermediates within the chorismate biosynthetic pathway that had been adversely affected in the aro mutant bacterium.

Chorismate Pathway:

Chorismate is a central intermediate in the biosynthesis of phenylalanine, tyrosine, tryptophan, folic acid, ubiquinone, and enterobactin (a siderophore) [see, Moat et al., *Microbial Physiology* (2002) Wiley-Liss, Chapter 15, pgs. 525-527]. The reactants, genes encoding the relevant enzymes, and the products of the metabolic pre-chorismate biosynthetic pathway starting from the combination of D-erythrose-4-phosphate with phosphoenol pyruvate, and ending with the biosynthesis of chorismate are provided below:

Where:
PEP is phosphoenol pyruvate;
DAHP is 3-hydroxy-L-arabino-heptulosonate 7-phosphate;
3-P-Shikimate is 3-phospho-shikamate; and
EEPK is 3-enoyl-pyruvyl-3-phosphoshikimate.

| Reactant(s) | Gene(s) | Product(s) |
|---|---|---|
| D-Erythrose-4-phosphate + PEP | - - aro (F, G, H) - → | DAHP |
| DAHP | - - aro B - → | 3-Dihydroquinate |
| 3-Dihydroquinate | - - aro D - → | 3-Dihydro-shikimate |

-continued

| Reactant(s) | Gene(s) | Product(s) |
|---|---|---|
| 3-Dihydro-shikimate | - - aro E - → | Shikimate |
| Shikimate + ATP | - - aro (K, L) - → | 3-P-Shikimate + ADP |
| 3-P-Shikimate + PEP | - - aro A - → | EEPK |
| EEPK | - - aro C - → | Chorismate |

As can be seen, the following order of aro genes (encoding isozymes from F, G, H), B, D, E, (encoding isozymes from K, L), A, and C are involved in the chorismate synthesis in *B. bronchiseptica*. There appear to be no by-passes in the biosynthesis of chorismate in *B. bronchiseptica*. Therefore, inactivation of any one of these aro genes or corresponding gene products, should lead to the identical blockade in the biosynthesis of key aromatic compounds.

In particular embodiments, the aro mutant of the *B. bronchiseptica* bacterium is an aroA mutant, although a deletion in other aro genes of *B. bronchiseptica* can lead to the same blockade in chorismate synthesis, as noted above, and thus to the same phenotype of the mutant bacterium.

Vaccines

The present invention provides safe and efficacious vaccines that comprise live attenuated bacteria for systemic administration. It is contemplated that such vaccines may further comprise one or more conventional pharmaceutically acceptable carriers, including adjuvants (see below), other immune-response enhancers, and/or vehicles (collectively referred to as "excipients"). Such excipients are generally selected to be compatible with the active ingredient(s) in the vaccine. The use of excipients is generally known to those skilled in the art of vaccine development.

Stabilizer components may include: sugars and sugar alcohols (such as sucrose, dextrose, trehalose, sorbitol), gelatin protein hydrolysates (lactalbumin hydrolysate, NZ Amine), serum albumin (bovine serum albumin, ovalbumin), and buffering compounds. Optionally and/or in addition, other substances such as stabilizers and viscosity modifiers may be added to a vaccine depending on the intended use or required properties of the vaccine. Many forms of vaccines are suitable for systemic vaccination, such as liquid formulations with dissolved, emulsified, or suspended antigens, and solid formulations such as implants or a solid antigen carrier suspended in a liquid. Systemic vaccination and suitable physical forms of vaccines for such vaccination have been known for many years.

It is also contemplated that the vaccine may be freeze-dried (lyophilized) or otherwise reduced in liquid volume for storage and then reconstituted in a liquid diluent before or at the time of administration. Such reconstitution may be achieved using, for example, vaccine-grade water. In certain embodiments, as exemplified below, a lyophilized portion of a multivalent vaccine can comprise one or more antigens, while the diluent can comprise one or more different antigens.

In particular embodiments, a vaccine of the present invention (or a portion thereof) can be in a freeze-dried form. Examples of such freeze-dried forms include: cakes, tablets, spheres, and/or ellipsoids, with the latter three forms being capable of being produced by a method described in WO 2010/125084, hereby incorporated by reference in its entirety. In particular, reference is made to the examples, from page 15, line 28 to page 27, line 9 of WO 2010/125084, describing a method to produce such fast disintegrating tablets/spheres/ellipsoids. Such freeze-dried forms can be readily dissolved in a diluent to enable systemic administration of the vaccine. Such diluents also can further comprise one or more additional active components of the vaccine.

Adjuvants:

As indicated above, the vaccines of the present invention can include an adjuvant. In more particular embodiments, the adjuvant comprises an aluminum salt. The use of aluminum salts as adjuvants is well known in the art of vaccine development. Aluminum salts have been developed in particular for toxoid based vaccines, but have also been used in conjunction with other subunit vaccines and vaccines containing inactivated (whole) micro-organisms. The use of aluminum salts in conjunction with live viral vaccines also has been described, though aluminum salts are typically not used to improve the efficacy of live bacterial vaccines. Surprisingly however, the fact that aluminum salts may bind live *B. bronchiseptica* appears to have no negative effect on the adjuvanting properties of these salts for a live *B. bronchiseptica* aro mutant strain. This, in combination with the well-known safety record of such adjuvants, makes their application preferable over other adjuvants such as hydrocarbon oils, saponins, etc. In an improved embodiment, the aluminum salt is chosen from the group consisting of aluminum phosphate, aluminum potassium phosphate, and aluminum hydroxide.

The optimum amount of adjuvant to add to a given vaccine of the present invention can vary depending on a number of variables such the antigens present in the vaccine and the species being vaccinated, but can be readily determined by one skilled in the art of vaccine development with the aid of the instant disclosure. In certain embodiments of the present invention, the amount of aluminum hydroxide, aluminum potassium sulfate, and/or aluminum phosphate in the vaccine can be between 0.5 to 15%. In more particular embodiments, the amount of aluminum hydroxide, aluminum potassium sulfate, and/or aluminum phosphate can be between 1.0 to 10%, and in even more particular embodiments, the amount of aluminum hydroxide, aluminum potassium sulfate, and/or aluminum phosphate in the vaccine can between 1.5 to 7.5%. As exemplified below, the amount of aluminum hydroxide or aluminum phosphate in the vaccine was about 2%, or alternatively about 5%.

aroA Mix:

As indicated above, the aro mutant bacterial vaccines of the present invention can include an aromatic supplement. The aromatic supplement can comprise one or more aromatic compounds. Examples of such aromatic compounds include but are not limited to: phenylalanine, tyrosine, tryptophan, prephenate, anthranilate, indole, para-amino benzoic acid, folic acid, 2,3-dihydroxybenzoate, and enterobactin [see, e.g., Moat et al., *Microbial Physiology* (2002) Wiley-Liss, Chapter 15, pgs. 525-527]. An aromatic supplement can also comprise an alternative source for chorismate and/or an alternative source for one or more intermediates within the chorismate biosynthetic pathway that had been adversely affected in the aroA mutant strain. In certain embodiments, an antioxidant and/or a chelating agent can be included with the aromatic supplement.

The optimum amount for the aromatic compounds comprised in the aromatic supplement that is to be added to a given vaccine of the present invention can vary depending on a number of variables such as the aromatic compounds themselves, the solvent system used with the aromatic compounds, the antigens present in the vaccine, and the species being vaccinated, but can be readily determined by one skilled in the art of vaccine development, with the aid of the instant disclosure. In certain embodiments of the present invention, the amount of each aromatic amino acid in the vaccine of the aromatic supplement can vary from 4 µg/mL to 0.4 mg/mL. In particular embodiments, the amount of each aromatic amino acid in the vaccine can vary from 10 µg/mL to 0.2 mg/mL. In more particular embodiments, the amount of each aromatic amino acid in the vaccine can vary from 20 µg/mL to 0.1 mg/mL. In even more particular embodiments, the amount of each aromatic amino acid in the vaccine can vary from 30 µg/mL to 60 µg/mL. As exemplified below, the individual amounts of phenylalanine, tyrosine, and tryptophan in the vaccine was about 40 µg/mL.

In certain embodiments of the present invention, the amount of any given aromatic compound in the vaccine that is not in the biosynthetic pathway of the aromatic amino acids can vary from 1 µg/mL to 0.1 mg/mL. In particular embodiments, the amount of such aromatic compounds can vary from 2.5 µg/mL to 50 µg/mL in the vaccine. In more particular embodiments, the amount of such, aromatic compounds in the vaccine can vary from 5 µg/mL to 20 µg/mL in the vaccine. As exemplified below, the individual amounts of 2,3-dihydroxybenzoic acid and para-aminobenzoic acid in the vaccine was 5 to 10 µg/mL.

Multivalent Vaccines:

The present invention also provides multivalent vaccines. In one embodiment, a vaccine comprising a live attenuated aro mutant of *B. bronchiseptica* of the present invention additionally comprises a canine influenza virus (CIV) antigen and/or a canine parainfluenza virus (CPI) antigen. A vaccine according to this embodiment should provide protection against kennel cough and/or canine infectious respiratory disease (CIRD) complex in dogs.

Examples of other antigens that can be combined with the live attenuated aro mutant *B. bronchiseptica* strain of the present invention (and/or another live attenuated aro mutant *B. bronchiseptica* strain) and/or canine influenza virus antigen and/or canine parainfluenza virus antigen to form a multivalent vaccine include one or more of the following: canine distemper virus, canine adenovirus type 2, canine parvovirus, canine pneumovirus, canine coronavirus, canine herpes virus, rabies virus, a *Mycoplasma* species, *Ehrlichia canis*, an *Anaplasma* species, *Leptospira canicola*, *Leptospira grippotyphosa*, *Leptospira hardjo*, *Leptospira icterohaemorrhagiae*, *Leptospira pomona*, *Leptospira interrogans*, *Leptospira autmnalis*, *Leptospira bratislava*. In addition, a vaccine comprising a live attenuated aro mutant *B. bronchiseptica* strain of the present invention can comprise one or more of the following feline pathogens: a feline herpesvirus (FHV), feline calicivirus (FCV), feline pneumovirus (FPN), *Chlamydophila felis*, feline parvovirus (FPV), feline leukemia virus (FeLV), feline infectious peritonitis virus (FIPV), feline immunodeficiency virus (FIV), borna disease virus (BDV), feline influenza virus, avian influenza, and *Bartonella* spp. (e.g., *B. henselae*).

Use of the aroA *B. Bronchiseptica* Mutant as a Recombinant Vector.

The construction of live avirulent mutant *Bordetella* vectors has been reported [see, e.g., US2008/0254062], including the use of a recombinant aroA mutant *B. bronchiseptica* vector in a vaccine [Stevenson and Roberts, *Vaccine* 20, 2325-2335 (2002); Stevenson and Roberts, *FEMS Immunology and Medical Microbiology* 37:121-128 (2003); Stevenson and Roberts, *Vaccine* 22:4300-4305 (2004)]. Therefore, methodology for making such constructs already has been provided.

Furthermore, inserting a heterologous nucleic acid (DNA) into an aroA mutant *B. bronchiseptica* strain of the present invention to express the corresponding heterologous antigen is readily accomplished, for example, when the termini of both the heterologous nucleic acid and the *B. bronchiseptica* comprise compatible restriction sites. Alternatively, it may be necessary to modify the termini of the heterologous nucleic acid and/or *B. bronchiseptica* by digesting back single-stranded DNA overhangs generated by restriction endonuclease cleavage to produce blunt ends, or to achieve the same result by filling in the single-stranded termini with an appropriate DNA polymerase. In still another methodology, desired sites may be produced, e.g., by ligating nucleotide sequences (linkers) onto the termini. Such linkers may comprise specific oligonucleotide sequences that define desired restriction sites. Restriction sites can also be generated through the use of the polymerase chain reaction (PCR) [see, e.g., Saiki et al., *Science* 239:487 (1988)]. The cleaved vector and the nucleic acid fragments may also be modified, if required, by homopolymeric tailing.

The heterologous nucleic acid can be operatively linked to either an endogenous or a heterologous promoter (i.e., endogenous to the recombinant *B. bronchiseptica*). Accordingly, the heterologous nucleic acid can either include its own naturally occurring promoter, or be modified to include a promoter (e.g., a bacterial promoter such as an *E. coli* lac promoter, which may be constitutive), that expresses the antigen it encodes. Notably, Stevenson and Roberts, [*Vaccine* 22:4300-4305 (2004)] specifically exemplified the use of the filamentous hemagglutinin (fha) promoter from *B. bronchiseptica*. Alternatively, the heterologous nucleic acid can be placed into the live aroA mutant *B. bronchiseptica* so as to allow a promoter already present in the aroA mutant *B. bronchiseptica* to express the heterologous antigen.

The heterologous nucleic acid can encode an antigen derived from any of a number of pathogens and includes, but is not restricted to, canine influenza virus, canine parainfluenza virus, canine distemper virus, canine adenovirus type 2, canine parvovirus, canine pneumovirus, rabies virus, canine coronavirus, *Mycoplasma* species, *Ehrlichia canis*, *Anaplasma* species, feline herpesvirus (FHV), feline calicivirus (FCV), feline pneumovirus (FPN), feline influenza virus, and/or *Chlamydophila felis*.

In embodiments contemplated by the present invention, the heterologous nucleic acid encodes a protein antigen from a feline or canine pathogen, as listed above. In more particular embodiments, the protein antigen is obtained from a canine influenza virus [see, U.S. Pat. No. 7,959,929 B2, the contents of which are hereby incorporated by reference in its entirety]. In other embodiments, the protein antigen is obtained from a feline influenza virus. In certain embodiments of this type, the heterologous nucleic acid encodes a hemagglutinin of the canine influenza virus. In particular embodiments of this type, the heterologous nucleic acid encodes a neuraminidase of the canine influenza virus. In still other embodiments of this type the heterologous nucleic acid encodes both a hemagglutinin and a neuraminidase of the canine influenza virus.

As used herein the term "polypeptide" is used interchangeably with the term "protein" and is further meant to encompass peptides. Therefore, as used herein, a polypeptide is a polymer of two or more amino acids joined together by peptide linkages. Preferably, the term "polypeptide" is directed towards a polymer comprising twenty or more amino acid residues joined together by peptide linkages, whereas a peptide comprises two to twenty amino acid residues joined together by peptide linkages.

As used herein the term "antigenic fragment" in regard to a particular protein is a fragment of that protein (including large fragments that are missing as little as a single amino acid from the full-length protein) that is antigenic, i.e., capable of specifically interacting with an antigen recognition molecule of the immune system, such as an immunoglobulin (antibody) or T cell antigen receptor.

A "polynucleotide" or a "nucleic acid" is a molecule comprising nucleotides including, but is not limited to, RNA, cDNA, genomic DNA and even synthetic DNA sequences. The terms are also contemplated to encompass nucleic acids that include any of the art-known base analogs of DNA and RNA.

A "heterologous nucleotide sequence" as used herein is a nucleotide sequence that is added to a nucleotide sequence and/or genome by recombinant methods to form a construct that is not naturally formed in nature. Such nucleic acids can also encode fusion (e.g., chimeric) proteins. Heterologous nucleotide sequences can encode peptides and/or proteins that contain antigenic, regulatory, and/or structural properties. A heterologous nucleotide sequence can comprise non-coding sequences including restriction sites, regulatory sites, promoters and the like.

As used herein, the terms "operably linked" and "operatively linked" are used interchangeably and refer to an arrangement of genetic elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. For example, intervening untranslated yet transcribed sequences can be present between a promoter and the coding sequence and the promoter can still be considered "operably linked" to the coding sequence.

As used herein, the terms "control sequence" and "control element" are used interchangeably. Transcriptional and translational control sequences are DNA regulatory sequences, such as promoters, enhancers, terminators, and the like, that provide for the expression of a coding sequence in a host cell. In eukaryotic cells, polyadenylation signals are control sequences. A coding sequence is operably linked to an expression control sequence when the expression control sequence controls or regulates the transcription and translation of that nucleotide sequence. The term operably linked can include having an appropriate start signal.

A coding sequence is "under the control" of transcriptional and translational control sequences in a cell when RNA polymerase transcribes the coding sequence into mRNA, which can then be trans-RNA spliced, if, when, and where appropriate, and translated into the protein encoded by the coding sequence.

Vaccine Administration:

The vaccines (including multivalent vaccines) of the present invention may be administered, e.g., systemically administered, as part of a combination therapy, i.e., a therapy that includes, in addition to the vaccine itself, administering one or more additional active agents, therapies, etc. In that instance, it should be recognized the amount of vaccine that constitutes a "therapeutically effective" amount may be more or less than the amount of vaccine that would constitute a "therapeutically effective" amount if the vaccine were to be administered alone. Other therapies may include those known in the art, such as, e.g., anti-viral medications, analgesics, fever-reducing medications, expectorants, anti-inflammation medications, antihistamines, antibiotics to treat *B. bronchiseptica* infection, and/or administration of fluids. In some embodiments, a vaccine of the present invention is administered in combination with one or more of the following: an influenza vaccine, parainfluenza vaccine, feline herpesvirus vaccine, feline calicivirus vaccine, Chlamydophlia vaccine, rhinotracheitis vaccine, panleukopenia vaccine, immunodeficiency virus vaccine, leukemia virus vaccine, or rabies vaccine. In specific embodiments, a vaccine of the present invention is administered subcutaneously (S/C).

The immunogenicity level may be determined experimentally by challenge dose titration study techniques generally known in the art. Such techniques typically include vaccinating a number of animal subjects with the vaccine at different dosages and then challenging the animal subjects with the virulent virus or bacterium to determine the minimum protective dose.

Factors affecting the preferred dosage regimen may include, for example, the species or breed (e.g., of a canine or feline), age, weight, sex, diet, activity, lung size, and condition of the subject; the route of administration; the efficacy, safety, and duration-of-immunity profiles of the particular vaccine used; whether a delivery system is used; and whether the vaccine is administered as part of a drug and/or vaccine combination. Thus, the dosage actually employed can vary for specific animals, and, therefore, can deviate from the typical dosages set forth above. Determining such dosage adjustments is generally within the skill of those in the art of vaccine development using conventional means. Under the specific conditions used in Example 4 below, a safe and effective dose of the aroA mutant *B. bronchiseptica* strain was determined to be between $5 \times 10^5$ to $5 \times 10^7$ cfu/mL, in the presence of an adjuvant and/or an aromatic supplement.

Similarly, the volume with which such a dose can be administered typically lies between 0.1 mL (typical for intradermal or transdermal application) and 5.0 mL. A typical range for the administration volume is between 0.2 and 2.0 mL, preferably about 1.0 to 2.0 mL for intramuscular or subcutaneous administration.

It is contemplated that the vaccine may be administered to the vaccine recipient at a single time or alternatively, two or more times over days, weeks, months, or years. In some embodiments, the vaccine is administered at least two times. In certain such embodiments, for example, the vaccine is administered twice, with the second dose (e.g., a booster) being administered at least 2 weeks after the first dose. In particular embodiments, the vaccine is administered twice, with the second dose being administered no longer than 8 weeks after the first dose. In other embodiments, the second dose is administered from 1 week to 2 years after the first dose, from 1.5 weeks to 8 weeks after the first dose, or from 2 to 4 weeks after the first dose. In other embodiments, the second dose is administered about 3 weeks after the first dose.

In the above embodiments, the first and subsequent dosages may vary, such as in amount and/or form. Often, however, the dosages are the same in amount and form. When only a single dose is administered, the amount of vaccine in that dose alone generally comprises a therapeutically effective amount of the vaccine. When, however, more than one dose is administered, the amounts of vaccine in those doses together may constitute a therapeutically effective amount. In addition, a vaccine may be initially administered, and then a booster may be administered from 2 to 12 weeks later, as discussed above. However, subsequent administrations of the vaccine may be made on an annual (1-year) or bi-annual (2-year) basis, regardless as to whether a booster was administered or not.

The present invention may be better understood by reference to the following non-limiting Examples, which are provided as exemplary of the invention. The following Examples are presented in order to more fully illustrate embodiments of the invention. They should in no way be construed, however, as limiting the broad scope of the invention.

EXAMPLES

Example 1

Construction of an aroA Mutant Strain of *Bordetella Bronchiseptica*

An aroA deletant mutant strain of *B. bronchiseptica* was constructed with the aim to formulate an efficacious vaccine with minimal side effects. A deletion in the aroA gene significantly impairs the ability of the *B. bronchiseptica* to grow without exogenously supplying one or more critical aromatic compounds.

The *B. bronchiseptica* strain used was originally isolated from a dog that was sick with upper respiratory disease. The aroA gene, which encodes an enzyme in the metabolic pathway required to synthesize essential aromatic compounds in *B. bronchiseptica* (see, above), along with adjacent sequences, was cloned by PCR from the chromosome of *B. bronchiseptica*. A ninety base-pair (bp) deletion was subsequently created by restriction digestion of the cloned gene with the enzyme Sal I. The deleted version of the aroA gene ($\Delta$aroA) was then reintroduced into *B. bronchiseptica* using vector tools and selection methods described for generating aroA deletant strains of *Mannheimia haemolytica*, *Pasteurella multocida*, and *Hemophilus somnus*. [Briggs, and Tatum, *Applied and Environmental Microbiology*, 71(11) 7187-7195 (2005); Tatum and Briggs, *Applied and Environmental Microbiology*, 71 (11) 7196-7202. (2005); U.S. Pat. No. 5,840,556, the contents of which are hereby incorporated by reference in their entirety.]

Briefly, these methods rely on the creation of temperature sensitive (Ts) versions of the origin of replication in plasmids found in *Mannheimia haemolytica*. These Ts plasmids cannot be effectively propagated at elevated temperatures ($\geq 39^\circ$ C.). These plasmids were further modified to contain kanamycin resistance and also an *E. coli* ColE1 origin of replication for propagation into *E. coli*. Once a plasmid containing the aroA is introduced into *B. bronchiseptica*, homologous recombination events occur between the native aroA region and those of the plasmid, such that portions of the plasmid will be introduced into the host *B. bronchiseptica* chromosome with a certain frequency. Selection of transformants with the antibiotic kanamycin enables isolation of these specific transformants. Confirmation of the insertion of the zaroA gene was accomplished by PCR and the DNA size was determined by agarose gel electrophoresis.

Removal of the undesired sequences from the chromosome, such as the native aroA gene, kanamycin resistance gene, and any other vector sequence, occurs by further recombination events. Selection of desired recombinants was accomplished by passage of cells without antibiotic at the non-permissive temperature for plasmid replication. Isolates that were kanamycin sensitive were screened by PCR and DNA agarose electrophoresis for the $\Delta$aroA gene and the absence of the native aroA gene. Sequence analysis of the *B. bronchiseptica* chromosome around the region of the aroA deletion was used to demonstrate that no foreign vector DNA was retained in the aroA mutant *B. bronchiseptica* isolate.

Example 2

Comparison of the Mouse $LD_{50}$ of the aroA Mutant Strain of *B. Bronchiseptica* to its Parent Non-Attenuated Strain Groups of eight mice were inoculated interperitoneally with a 0.5 mL dose of serial dilutions of either the aroA mutant strain of *B. bronchiseptica* (see, Example 1 above) or with its parent non-attenuated strain to determine their $LD_{50}$. The mice were observed for seven days with the number of dead mice recorded daily (see, Table 1 below). There was 100% mortality in the groups inoculated with $2.8 \times 10^7$ cfu/dose or more of the parent strain ($LD_{50}$ $8.9 \times 10^6$) and $1.2 \times 10^9$ cfu/dose or more of the aroA mutant strain ($LD_{50}$ $3.8 \times 10^8$). Notably, there were no deaths at lower dilutions of either the parent strain or the aroA mutant strain, respectively. These results demonstrate that the deletion in the aroA gene significantly attenuates *B. bronchiseptica*, making it approximately 40-fold less virulent in mice than the parent strain.

TABLE 1

Mortality of Mice Post-Inoculation

| Group | Strain | cfu/dose | Day 1 | Day 2 | Day 3 | Day 4 | Day 5 | Day 6 | Day 7 | Total |
|---|---|---|---|---|---|---|---|---|---|---|
| A1 | Parent | $2.8 \times 10^8$ | 1 | 7 | — | — | — | — | — | 8/8 |
| A2 | Parent | $2.8 \times 10^7$ | 0 | 1 | 4 | 2 | 1 | — | — | 8/8 |
| A3 | Parent | $2.8 \times 10^6$ | 0 | 0 | 0 | 0 | 0 | 0 | 0 | 0/8 |
| A4 | Parent | $2.8 \times 10^5$ | 0 | 0 | 0 | 0 | 0 | 0 | 0 | 0/8 |
| A5 | Parent | $2.8 \times 10^4$ | 0 | 0 | 0 | 0 | 0 | 0 | 0 | 0/8 |
| B1 | $\Delta$aroA | $1.2 \times 10^{10}$ | 8 | — | — | — | — | — | — | 8/8 |
| B2 | $\Delta$aroA | $1.2 \times 10^9$ | 0 | 8 | — | — | — | — | — | 8/8 |
| B3 | $\Delta$aroA | $1.2 \times 10^8$ | 0 | 0 | 0 | 0 | 0 | 0 | 0 | 0/8 |
| B4 | $\Delta$aroA | $1.2 \times 10^7$ | 0 | 0 | 0 | 0 | 0 | 0 | 0 | 0/8 |
| B5 | $\Delta$aroA | $1.2 \times 10^6$ | 0 | 0 | 0 | 0 | 0 | 0 | 0 | 0/8 |

Example 3

Determination of a Safe and Effective Vaccine Dose

In an effort to find a safe and effective dose range, an experimental vaccine comprising the aroA mutant ($\Delta$aroA) strain of *B. bronchispetica* of Example 1 was administered subcutaneously to dogs at three different (commonly applied) dosage levels. Accordingly, a 1 mL dose of the live culture of the $\Delta$aroA *B. bronchiseptica* strain was administered to Treatment Groups A, B, and C (8 dogs each) as follows: on study days 0 and 21, the bacteria were grown in Tryptose Phosphate Broth (TPB) for 12 hours and then diluted to the target doses of $1.0 \times 10^8$ cfu/mL (Group A), $1.0 \times 10^7$ cfu/mL (Group B), and $1.0 \times 10^6$ cfu/mL (Group C), respectively. The dogs in control Group D (9 dogs) received sterile TPB.

Vaccination

Each dog was vaccinated subcutaneously at the base of the neck with a 1 mL dose of the respective vaccine on study days 0 and 21 using a syringe with a sterile 22G 1" needle. The first vaccination was on the right side and the second vaccination on the left side. Bacterial plate counts were performed before and after each vaccination to determine the dose given.

Post-Vaccination Monitoring

Following vaccination, whole blood was collected to determine antibody titers. Injection sites were palpated daily until no injection site reaction could be felt. The height, width, and depth of an injection site reaction was measured in centimeters (cm) using calipers. The injection site reaction was further characterized as thickening, soft, hard, or tender.

Challenge

The challenge was performed with the following material. *B. bronchiseptica* strain D-2 [Musser et al., *Journal of Bacteriology*, 169(6):2793-2803 (June 1987)] was inoculated onto Tryptose Phosphate Broth (TPB) agar plates (200 µL per plate), and the plates were incubated for approximately 16-18 hrs at 36±2° C. The pure bacterial growth was washed off the agar plates with 10 mL of TPB per plate and the density adjusted to ≥1.0×10$^{10}$ cfu/mL. Fresh challenge material was prepared for each day of challenge. On study days 35 and 36, intranasal administration of the challenge material was performed by instilling 0.5 mL per nare using a 3 mL syringe with an applicator.

Post-Challenge Monitoring

Dogs were observed daily for 21 days post-challenge for clinical signs including, but not limited to, depression, lethargy, inappetence, coughing, nasal discharge, and dyspnea. The dogs received gentle tracheal palpation daily in attempt to induce coughing. The clinical signs "mucoid discharge", "mucopurulent nasal discharge", "induced cough", "spontaneous cough", "spontaneous cough with retching", and "dyspnea" were scored. Nasal swabs were collected from each dog twice a week for three weeks to determine shedding of the challenge organisms.

Data Analysis:

The primary outcome variables were clinical signs of disease and/or bacterial shedding. The experimental unit in this study was the individual dog. Numeric scores were assigned for behavioral and physical traits according to the clinical observations. Clinical scores were summed for each dog, for each day, and the median score calculated. For shedding data, the mean cfu/mL of *B. bronchiseptica* organisms isolated from nasal swabs was calculated: (i) for each treatment group, (ii) for each nasal swab collection, and (iii) the number of days of shedding.

Results:

Prior to vaccination, all dogs had low antibody titers 64) to *B. bronchiseptica* and were negative for *B. bronchiseptica* infection as determined by nasal swab isolation. Vaccination with 1.0×10$^6$ cfu/mL *B. bronchiseptica* aroA-(Treatment Group C) and placebo (Treatment Group D) did not induce an increase in antibodies specific for *B. bronchiseptica*. In contrast, vaccination with a dose of 1.0×10$^8$ (Treatment Group A) induced antibody titers of 256 or greater in 100% (8/8) of the dogs, and vaccination with a dose of 1.0×10$^7$ cfu/mL induced antibody titers of 128 or greater in 25% (2/8) of the dogs on study day 28. The geometric mean for Treatment Groups A, B, C, and D on study day 28 was 470, 76, 35, and 40, respectively (Table 2).

TABLE 2

Pre-/Post- Vaccination Geometric Mean Serum Antibody Titers to *B. bronchiseptica*

| Treatment Group | Study Day −4 | Study Day 20 | Study Day 28 |
|---|---|---|---|
| A<br>1.0 × 10$^8$ cfu/mL | 17 | 70 | 470 |
| B | 25 | 41 | 76 |
| 1.0 × 10$^7$ cfu/mL<br>C | 29 | 35 | 35 |
| 1.0 × 10$^6$ cfu/mL<br>D<br>placebo | 25 | 30 | 40 |

Dogs in Treatment Group A developed a swelling at the injection site that resolved within 9-13 days post-vaccination. The largest injection site reaction measured in Treatment Group A was 2×2×1.5 cm, and 2 of the 8 dogs had injection site reactions that were tender upon palpation. Dogs in Treatment Group B developed a swelling at the injection site that resolved within 3-6 days post-vaccination, with the largest injection site reaction measuring 2×2×1.5 cm. Only one dog developed a slight swelling in Treatment Group C (0.5×0.5×0.5 cm), which was only measurable for one day. No injection site reactions were observed in Treatment Group D. The mean injection site reaction for each treatment group as calculated using the largest size injection site reaction for each dog following the first vaccination is shown in Table 3. Although none of the vaccines caused any harmful systemic reactions following vaccination, the size and character of the swellings in Groups A and B would not be commonly acceptable in veterinary practice.

TABLE 3

Mean Injection Site Reaction Sizes

| Treatment Group | Mean Injection Site Reaction Size (cm$^2$) |
|---|---|
| A<br>1.0 × 10$^8$ cfu/mL | 2.1 |
| B<br>1.0 × 10$^7$ cfu/mL | 1.0 |
| C<br>1.0 × 10$^6$ cfu/mL | 0 |
| D<br>placebo | 0 |

Following challenge, the clinical signs were scored for each dog and summed over a 21-day observation period. Vaccination with the *B. bronchiseptica* aroA-strain at 1.0×10$^8$ cfu/mL and 1.0×10$^7$ cfu/mL reduced the clinical signs associated with a *B. bronchiseptica* infection. Seven of nine (78%) dogs in the placebo-vaccinated control group (Treatment Group D) and five of eight (63%) dogs in Treatment Group C (1.0×10$^6$ cfu/mL) had cough scores of 1 or higher during the 21-day observation period; whereas, only one of eight (13%) dogs vaccinated with 1.0×10$^8$ cfu/mL (Treatment Group A) and two of eight (25%) dogs in Treatment Group B had cough scores of 1 or higher for one day during the 21-day observation period. The median clinical score is depicted in Table 4 for each group of dogs vaccinated with the live aroA mutant *B. bronchiseptica* strain of Example 1 and then challenged with virulent *B. bronchiseptica*.

Nasal swabs were collected at six time points during the 21 day post-challenge observation period to determine shedding of challenge organisms. At 21 days-post-challenge, all the dogs (100%) in Treatment Groups C and D were shedding large numbers of *B. bronchiseptica*, compared to four of eight (50%) dogs still shedding in Treatment Group A and five of eight (63%) in Treatment Group B. The mean number of *B.* bronchiseptica organisms isolated from the noses of dogs in Groups A, B, and C was less than the mean number of organisms isolated from dogs in Group D (Table 4).

TABLE 4

Post-Challenge Clinical Scores and B. bronchiseptica Shedding

| Treatment Group | Median Clinical Score | No. of Dogs with Cough Scores ≥1 | Mean No. of B. bronchiseptica Organisms Shed |
|---|---|---|---|
| A<br>$1.0 \times 10^8$ cfu/mL | 0 | 1/8 (13%) | 2261 |
| B<br>$1.0 \times 10^7$ cfu/mL | 0.5 | 2/8 (25%) | 32,592 |
| C<br>$1.0 \times 10^6$ cfu/mL | 3.5 | 5/8 (63%) | 46,341 |
| D<br>placebo | 3.0 | 7/9 (78%) | 73,656 |

In conclusion, a live aroA mutant strain of B. bronchiseptica can be used as a live vaccine for systemic administration to canines. However, at titers in which the live aroA mutant strain of B. bronchiseptica was most efficacious, the vaccines also caused unacceptable injection site reactions.

Example 4

Improvement of Efficacy at a Safe Level

A subsequent study was conducted to assess whether the efficacy of the lowest dose tested ($1 \times 10^6$ cfu) could be significantly improved, while maintaining minimal, if any, injection site reactions. The experimental vaccines for new Treatment Groups A, B, C, and D (5 dogs each) contained a live culture of the aroA mutant B. bronchiseptica strain of Example 1 administered in a 1 mL dose. Dogs in Treatment Group E received sterile DMEM without any antigen. The aroA mutant B. bronchiseptica strain was grown in Tryptose Phosphate Broth (TPB) for 17 hours in a 5 L fermentor and harvested when the $OD_{580\,nm}$ was 1.0 to 2.0. The fermentation culture was blended with stabilizer and lyophilized.

The lyophilized cakes were rehydrated to a target dose of $1.0 \times 10^8$ cfu/mL with sterile water for Treatment Group A. For Treatment Groups B, C, and D the lyophilized cakes were rehydrated to a target dose of $1.0 \times 10^6$ cfu/mL with sterile water:
  plus 2% aluminum phosphate for Group B;
  plus 2% aluminum hydroxide for Group C; or
  plus the aromatic compound mix for Group D.

The lyophilized cakes for Treatment Group E were rehydrated with sterile water, see Table 6 below.

The 2% aluminum phosphate adjuvant used was 2% Rehydraphos®, whereas the 2% aluminum hydroxide adjuvant used was 2% Rehydrogel® LV. Both of these adjuvants are commercially available from Reheis Inc., Berkeley Heights, N.J., USA. The aromatic compound mix (aromatic supplement) is described in Table 5 below. On study days 0 and 21 the dogs were vaccinated with the above vaccines or the DMEM placebo.

TABLE 5

Aromatic Compound Mix

| Component | Aromatic Supplement (µg/mL) |
|---|---|
| L-Tyrosine | 40 |
| 2,3-Dihydroxybenzoic acid | 5 |
| L-Tryptophan | 40 |
| L. Phenylalanine | 40 |
| Para-Aminobenzoic Acid | 10 |

Vaccination

Each dog was vaccinated subcutaneously at the base of the neck with a 1 mL dose of the respective vaccine on study days 0 and 21 using a syringe with a sterile 22G 1" needle. The first vaccination was on the right side and the second vaccination on the left side. Bacterial plate counts were performed before and after each vaccination to determine the dose given.

Post-Vaccination Monitoring

Following vaccination, whole blood was collected to determine antibody titers. Injection sites were palpated daily until no injection site reaction could be felt. The height, width, and depth of an injection site reaction was measured in centimeters (cm) using calipers. The injection site reaction was further characterized as thickening, soft, hard, or tender.

Challenge

Challenge was performed with the following material. B. bronchiseptica strain D-2 was inoculated onto Tryptose Phosphate Broth (TPB) agar plates (200 µL per plate), and the plates were incubated for approximately 16-18 hrs at 36±2° C. The pure bacterial growth was washed off the agar plates with 10 mL of TPB per plate and the density adjusted to $\geq 1.0 \times 10^{10}$ cfu/mL. Fresh challenge material was prepared for each day of challenge. On study day 42 fresh challenge culture was administered intranasally by instilling 0.5 mL per nare using a 3 mL syringe with an applicator. On study day 43, fresh challenge culture was administered intranasally by instilling 0.5 mL per nare using an atomizer with an electric pump.

Post-Challenge Monitoring

Dogs were observed daily for 21 days post-challenge for clinical signs including, but not limited to, depression, lethargy, inappetence, coughing, nasal discharge, and dyspnea. The dogs received gentle tracheal palpation daily in attempt to induce coughing. The clinical signs "mucoid discharge", "mucopurulent nasal discharge", "induced cough", "spontaneous cough", "spontaneous cough with retching" and "dyspnea" were scored.

Results

Prior to vaccination, all dogs had low antibody titers (≤64) to B. bronchiseptica and were negative for B. bronchiseptica infection as determined by nasal swab isolation. The control dogs (Treatment Group E) had antibody titers of 32 or less in 100% (five of five) of the dogs at study day 28. In contrast, vaccination with the aroA mutant B. bronchiseptica strain at $1.0 \times 10^6$ cfu/mL (Treatment Group A) induced antibody titers of 256 or greater in 80% (four of five) of the dogs, vaccination with $1.0 \times 10^6$ cfu/mL+2% Rehydraphos® (Treatment Group B) induced antibody titers of 128 or greater in 80% (four of five) of the dogs, vaccination with $1.0 \times 10^6$ cfu/mL+2% Rehydragel® LV (Treatment Group C) induced antibody titers of 128 or greater in 40% (two of five) of the dogs, and vaccination at $1.0 \times 10^6$ cfu/mL+1×AroMix (Treatment Group D) induced antibody titers of 128 or greater in 60% (three of five) of the dogs. The geometric mean titer for Treatment Groups A, B, C, D, and E on study day 28 was 338, 111, 84, 97, and 14, respectively (Table 6).

TABLE 6

Pre-/Post- Vaccination Geometric Mean Serum Antibody Titers to *B. bronchiseptica*

| Treatment Group | cfu | Addition | Study Day −4 | Study Day 20 | Study Day 28 |
|---|---|---|---|---|---|
| A | $1 \times 10^8$ | — | 37 | 64 | 338 |
| B | $1 \times 10^6$ | 2% aluminum phosphate | 32 | 49 | 111 |
| C | $1 \times 10^6$ | 2% aluminum hydroxide | 32 | 37 | 84 |
| D | $1 \times 10^6$ | aromatic compound mix | 32 | 56 | 97 |
| E | — | — | 28 | 28 | 14 |

Dogs remained clinically normal following vaccination, including no fevers. Dogs in Treatment Group A developed a moderate swelling at the injection site that resolved within 16-19 days post-vaccination. The largest reaction measured in Treatment Group A was 3.0×3.0×0.5 cm, and three of the five dogs had reactions that were tender upon palpation. Dogs (four of five) in Treatment Group B developed a slight swelling at the injection site that resolved within 9-11 days post-vaccination, with the largest reaction measuring 1.0×1.0×0.5 cm, and one of the five dogs had a reaction that was tender upon palpation. Dogs (five of five) in Treatment Group C developed a slight swelling at the injection site that resolved within 9-10 days post-vaccination, with the largest reaction measuring 1.0×1.0×0 cm. Only two of five dogs in Treatment Group D developed a slight swelling at the injection site that resolved within 5-8 days post-vaccination, with the largest reaction measuring 0.5×0.5×0 cm. No injection site reactions were observed in Treatment Group E. The mean injection site reaction for each treatment group as calculated using the largest size injection site reaction for each dog following the first vaccination is shown in Table 7. These results confirm previous observations that a vaccine dose of $1.0 \times 10^8$ cfu/mL is not safe for use in young dogs; whereas a dose of $1 \times 10^6$ cfu/mL, even when administered with adjuvant, provides a better safety profile that would be considered acceptable in veterinary practice.

TABLE 7

Mean Injection Site Reaction Sizes

| Treatment Group | cfu | Addition | Mean Injection Site Reaction Size (cm²) |
|---|---|---|---|
| A | $1 \times 10^8$ | — | 4.5 |
| B | $1 \times 10^6$ | 2% aluminum phosphate | 0.2 |
| C | $1 \times 10^6$ | 2% aluminum hydroxide | 0.4 |
| D | $1 \times 10^6$ | aromatic compound mix | 0.1 |
| E | — | — | 0 |

Following challenge, the clinical signs were scored for each dog and summed over a 21-day observation period. The challenge dose was judged to be adequate to determine the efficacy of the vaccines because at least 50% of the control dogs showed clinical signs of disease and/or bacterial shedding. A dog was defined as having developed a persistent cough (an affected dog) if spontaneous coughing or spontaneous coughing with retching was observed on ≥3 non-consecutive days during the post-challenge observation period. As shown in Table 8, the addition of either an adjuvant or the aromatic compound mix (aromatic supplement) to a vaccine comprising a titer of $1 \times 10^6$ cfu of the aroA mutant *B. bronchiseptica* strain resulted in protection to vaccinated dogs against a challenge with virulent *B. bronchiseptica*. Four of the five placebo-vaccinated control dogs developed a persistent cough following challenge, compared to none of the dogs in Treatment Groups A, B, and D, and only 1 dog in Treatment Group C. The median clinical score for Treatment Groups A, B, C, D, and E was 2, 1, 3, 1, and 13, respectively (Table 8).

Nasal swabs were collected at six time points during the 21 day post-challenge observation period to determine shedding of challenge organisms. At 21 days post-challenge (study day 63), all the dogs (100%) in Treatment Group E were shedding large numbers of *B. bronchiseptica*. The mean cfu/mL of *B. bronchiseptica* challenge organisms isolated from nasal swabs on study day 63 was 726, 5,048, 17,400, 594, and 135,840 for Treatment Group A, B, C, D, and E, respectively. The overall mean cfu/mL of *B. bronchiseptica* challenge organisms isolated from nasal swabs on all study days was 6,899, 3,662, 6,671, 8,060, and 24,067 for Treatment Group A, B, C, D, and E, respectively (Table 8).

TABLE 8

Post-Challenge Clinical Scores and *B. bronchiseptica* Shedding

| Treatment Group | cfu | Addition | Median Clinical Score | No. Of Affected Dogs* | Mean No. of *B. bronchiseptica* Organisms Shed |
|---|---|---|---|---|---|
| A | $1 \times 10^8$ | — | 2 | 0/5 (0%) | 6899 |
| B | $1 \times 10^6$ | 2% aluminum phosphate | 1 | 0/5 (0%) | 3662 |
| C | $1 \times 10^6$ | 2% aluminum hydroxide | 3 | 1/5 (20%) | 6671 |
| D | $1 \times 10^6$ | aromatic compound mix | 1 | 0/5 (0%) | 8060 |
| E | — | — | 13 | 4/5 (80%) | 24067 |

In conclusion, four different live attenuated aroA mutant *B. bronchiseptica* vaccine formulations were evaluated for safety and efficacy. Vaccines having a titer of $1 \times 10^6$ of the aroA mutant *B. bronchiseptica* strain plus either an aluminum hydroxide adjuvant, an aluminum phosphate adjuvant, or an aromatic supplement helped protect dogs from clinical signs of disease without causing significant swelling at the injection site. Therefore, the present study minimally demonstrates that the addition of an adjuvant and/or an aromatic supplement to a vaccine comprising a live attenuated aro mutant of *B. bronchiseptica* strain significantly decreases the dose necessary for that vaccine to be efficacious, which in turn, serves to minimize any resulting injection site reactions due to the administration of the vaccine.

Example 5

Vaccine Against *Bordetella Bronchiseptica*, Canine Influenza Virus, and Canine Parainfluenza Virus A multivalent vaccine has been formulated against canine influenza virus (CIV), canine parainfluenza virus (CPI), and *Bordetella bronchiseptica* (*B. bronchiseptica*). The canine vaccine comprises a modified live canine parainfluenza virus, a killed canine influenza virus, and the live attenuated aroA mutant strain of *B. bronchiseptica* as described in Example 1. The vaccine is designed for subcutaneous administration. The product is recommended as an aid in the prevention of disease caused by *B. bronchiseptica*, canine parainfluenza virus, and as an aid in the control of disease caused by canine influenza virus. Each dose of vaccine is to contain at least $10^{5.7}$ TCID$_{50}$ [50% Tissue Culture Infective Dose] of CPI, $1\times10^6$ cfu of *B. bronchiseptica*, and 1000 HAU [Hemagglutinin units] of CIV.

Production cultures of *B. bronchiseptica* were cooled in a fermentor, and an aromatic compound mix (aromatic supplement) as described in Table 9 below, was added to the culture. The modified live CPI was then blended with the live aroA mutant *B. bronchiseptica* strain, together with stabilizer, 5% glutathione solution, the aromatic compound mix (aromatic supplement) of Table 9, and DMEM media. This blend was then lyophilized and stored. The lyophilized cake was rehydrated in diluent containing the killed CIV and either 2% aluminum hydroxide adjuvant or 5% aluminum hydroxide adjuvant.

TABLE 9

| Aromatic Compound Mix | |
|---|---|
| Component | Volume (per Liter of Harvest) |
| L-tyrosine (16 mg/mL) | 2.5 mL |
| 2,3-dihydroxybenzoic acid (5 mg/mL) | 1 mL |
| L-tryptophan (4 mg/mL), L-phenylalanine (4 mg/mL), and para-aminobenzoic acid (1 mg/mL) | 10 mL |

Dogs in Treatment Groups B and C were vaccinated with a lyophilized vaccine containing the live aroA mutant *B. bronchiseptica* strain and CPI rehydrated to a target dose of $5.0\times10^5$ cfu/mL of the live aroA mutant *B. bronchiseptica* strain with sterile water:

plus CIV plus 2% aluminum hydroxide adjuvant for Group B; or plus CIV plus 5% aluminum hydroxide adjuvant for Group C.

Dogs in Treatment Group D were vaccinated with only CIV plus 2% aluminum hydroxide adjuvant. The aluminum hydroxide used in all three treatment groups was Rehydragel® LV.

Vaccination

Each dog was vaccinated by the subcutaneous route at the base of the neck with a 1 mL dose of the respective vaccine on study days 0 and 21 using a sterile 22G 1" needle. The first vaccination was on the right side and the second vaccination on the left side. Bacterial plate counts were performed before and after each vaccination to determine the dose given.

Post-Vaccination Monitoring

Whole blood was collected post-vaccination to determine antibody titers. Injection sites were palpated daily until no injection site reaction could be felt. The height, width, and depth of a injection site reaction was measured in centimeters (cm) using calipers and further characterized as thickening, soft, hard, or tender.

Challenge

Challenge was performed with the following material. *B. bronchiseptica* strain D-2 was inoculated onto Tryptose Phosphate Broth (TPB) agar plates (200 μL per plate), and the plates were incubated for approximately 16-18 hours at 36±2° C. The pure bacterial growth was washed off the agar plates with 10 mL of TPB per plate and the density adjusted to $\geq1\times10^{10}$ cfu/mL. Fresh challenge material was prepared for each day of challenge. On study day 35, the challenge material was administered by the intranasal route by instilling 0.5 mL per nare using a 3 mL syringe with an applicator. On study day 36, challenge material was administered by the intranasal route by instilling ~0.5 mL per nare using an atomizer and electric pump.

Post-Challenge Monitoring

Dogs were observed daily for 21 days post-challenge for clinical signs including, but not limited to, depression, lethargy, coughing, and nasal discharge. Nasal swabs were collected twice a week, 3-4 days between collections, for 3 weeks following challenge to determine shedding of challenge organisms.

Results

Prior to vaccination, all dogs had low antibody titers (≤64) to *B. bronchiseptica* and were negative for *B. bronchiseptica* infection as determined by nasal swab isolation. On study day 28, four of the five (80%) placebo-vaccinated control dogs (Treatment Group D) had antibody titers of 64 or less. In contrast, all the dogs that received the test vaccine containing $5.0\times10^5$ cfu/mL of the aroA mutant *B. bronchiseptica* strain, CPI, CIV, and 2% Rehydragel LV (Treatment Group B) or 5% Rehydragel LV (Treatment Group C) had antibody titers of 64 or greater. The geometric mean titer for Treatment Groups B, C, and D on study day 28 was 111, 111, and 64, respectively (Table 10).

TABLE 10

Pre-/Post- Vaccination Geometric Mean Serum Antibody Titers to *B. bronchiseptica*

| Treatment Group | *B. bronchiseptica* cfu | Additions to Vaccine | Study Day −1 | Study Day 28 |
|---|---|---|---|---|
| B | $5.0\times10^5$ | CPI, CIV, and 2% aluminum hydroxide | 28 | 111 |
| C | $5.0\times10^5$ | CPI, CIV, and 5% aluminum hydroxide | 42 | 111 |
| D | — | CIV and 2% aluminum hydroxide | 42 | 64 |

Dogs remained clinically normal following vaccination, including no fevers. Three of the five dogs in Treatment Group B had a slight swelling at the injection site that resolved within 1-5 days post-vaccination, with the largest injection site reaction measuring 1.0×1.0×0.5 cm. All dogs in Treatment Group C developed a slight swelling at the injection site that resolved within 7 to 11 days post-vaccination, with the largest injection site reaction measuring 1.0×1.0×0.5 cm. None of the five dogs in Treatment Group D developed injection site reactions following either vaccination. The mean injection site reaction for each treatment group as calculated using the largest size injection site reaction for each dog following the first vaccination is shown in Table 11.

TABLE 11

Mean Injection Site Reaction Sizes

| Treatment Group | *B. bronchiseptica* cfu | Additions to Vaccine | Mean Injection Site Reaction Size ($cm^2$) |
|---|---|---|---|
| B | $5.0\times10^5$ | CPI, CIV, and 2% aluminum hydroxide | 0.2 |
| C | $5.0\times10^5$ | CPI, CIV, and 5% aluminum hydroxide | 0.3 |

TABLE 11-continued Mean Injection Site Reaction Sizes

| Treatment Group | B. bronchiseptica cfu | Additions to Vaccine | Mean Injection Site Reaction Size ($cm^2$) |
|---|---|---|---|
| D | — | CIV and 2% aluminum hydroxide | 0 |

Following challenge, the clinical signs were scored for each dog and summed over a 21-day observation period. Four of the five placebo-vaccinated control dogs developed clinical signs of disease including spontaneous cough post-challenge, indicating a valid challenge. In contrast, the two test vaccines reduced the clinical signs associated with a *B. bronchiseptica* infection, specifically coughing, when compared to the control dogs. The median cough score for Treatment Groups B, C, and D was 1, 0, and 2, respectively (Table 12), and the percentage of dogs that developed clinical disease was 20%, 20%, and 40%, respectively.

Nasal swabs were collected at six time points during the 21-day post-challenge observation period to determine shedding of challenge organisms. At 21 days post-challenge (study day 55), all dogs (100%) in Treatment Group D were shedding large numbers of *B. bronchiseptica* organisms, whereas, there was notably less shedding in each of the two vaccinate groups. The mean cfu/mL of *B. bronchiseptica* D2 challenge organisms isolated from nasals swabs on study day 55 was 15,494, 26,802, and 150,620 for Treatment Groups B, C, and D, respectively. Overall, dogs in Treatment Group B shed fewer *B. bronchiseptica* organisms than dogs in Treatment Groups C and D. The overall mean cfu/mL of *B. bronchiseptica* D2 challenge organisms isolated from nasal swabs on all study days was 38,642, 206,713, and 178,609 for Treatment Groups B, C, and D, respectively (Table 12).

TABLE 12

Post-Challenge Clinical Scores and *B. bronchiseptica* Shedding

| Treatment Group | Vaccine | Median Clinical Score | % of Dogs with Clinical Disease | Mean No. Of B. bronchiseptica Organisms Shed |
|---|---|---|---|---|
| B | $5.0 \times 10^5$ cfu/mL B.b, CPI, CIV, and 2% aluminum hydroxide | 1 | 20% | 38,642 |
| C | $5.0 \times 10^5$ cfu/mL B.b, CPI, CIV, and 5% aluminum hydroxide | 0 | 20% | 206,713 |
| D | CIV and 2% aluminum hydroxide | 2 | 40% | 178,609 |

In conclusion, two different live attenuated aroA mutant *B. bronchiseptica*+CPI+CIV vaccine formulations were evaluated for safety and efficacy. Vaccines having a titer of $5\times10^5$ of the aroA mutant *B. bronchiseptica* strain plus an aromatic supplement and an aluminum hydroxide adjuvant at either 2% or 5%, helped protect dogs from clinical signs of disease without causing significant swelling at the injection site. Therefore, the present study minimally demonstrates that the addition of an adjuvant and an aromatic supplement to a vaccine comprising a live attenuated aro mutant of *B. bronchiseptica* strain significantly decreases the dose necessary for that vaccine to be efficacious, which in turn, serves to minimize any resulting injection site reactions due to the administration of the vaccine.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

We claim:

1. A vaccine for protecting an animal against a clinical disease arising from an infection with *Bordetella bronchiseptica* (*B. bronchiseptica*) comprising a live aro mutant *B. bronchiseptica* strain and an aromatic supplement; wherein the vaccine is suitable for systemic administration.

2. The vaccine of claim 1 wherein the aromatic supplement comprises tyrosine, tryptophan, and phenylalanine.

3. The vaccine of claim 2 wherein the aromatic supplement further comprises para-aminobenzoic acid.

4. The vaccine of claim 3 wherein the aromatic supplement further comprises 2,3-dihydroxybenzoic acid.

5. The vaccine of claim 1 wherein the live aro mutant *B. bronchiseptica* strain is a live aroA mutant *B. bronchiseptica* strain.

6. The vaccine of claim 5 that further comprises an adjuvant.

7. The vaccine of claim 6 wherein the adjuvant comprises an aluminum salt.

8. The vaccine of claim 7 wherein the aluminium salt is selected from the group consisting of aluminum phosphate, aluminum potassium sulfate, and aluminum hydroxide.

9. The vaccine of claim 8, that further comprises a canine influenza virus antigen, a canine parainfluenza virus antigen, or both a canine influenza virus antigen and a canine parainfluenza virus antigen.

10. The vaccine of claim 9 wherein the aromatic supplement comprises tyrosine, tryptophan, and phenylalanine.

11. The vaccine of claim 10 wherein the aromatic supplement further comprises para-aminobenzoic acid and 2,3-dihydroxybenzoic acid.

12. The vaccine of claim 5, that further comprises a canine influenza virus antigen, a canine parainfluenza virus antigen, or both a canine influenza virus antigen and a canine parainfluenza virus antigen.

13. The vaccine of claim 12 wherein the canine influenza virus antigen is a killed canine influenza virus and the canine parainfluenza virus antigen is a modified live canine parainfluenza virus.

14. The vaccine of claim 13, wherein the live aroA mutant *B. bronchiseptica* strain and the modified live canine parainfluenza virus are in freeze-dried spheres and the killed canine influenza virus is in a diluent.

15. A vaccine for protecting an animal against a clinical disease arising from an infection with *Bordetella bronchiseptica* (*B. bronchiseptica*) comprising a live aro mutant *B. bronchiseptica* strain and an adjuvant; wherein the vaccine is suitable for systemic administration; and wherein the adjuvant comprises an aluminium salt selected from the group consisting of aluminum phosphate, aluminum potassium sulfate, aluminum hydroxide, and a combination thereof; and wherein the amount of the aluminium salt in the vaccine is between 0.5 to 15%.

16. The vaccine of claim 15, wherein the aluminium salt in the vaccine is between 1.5 to 7.5% aluminum hydroxide.

17. A multivalent vaccine comprising a live aro mutant *Bordetella bronchiseptica* (*B. bronchiseptica*) strain that comprises a nucleic acid encoding canine influenza virus H3 hemagglutinin protein; wherein said nucleic acid is operably linked to a promoter; and whereby said live aro mutant *B. bronchiseptica* strain can express the canine influenza virus H3 hemagglutinin.

18. The multivalent vaccine of claim 17, wherein the multivalent vaccine further comprises an aromatic supplement.

19. A method of aiding in the protection of a canine against a clinical disease arising from an infection with *B. bronchiseptica* comprising administering systemically the vaccine of claim 11 to that canine.

20. A method of aiding in the protection of an animal against a clinical disease arising from an infection with *B. bronchiseptica* comprising administering systemically the vaccine of claim 1 to that animal.

21. An immunogenic composition comprising a live aro mutant *Bordetella bronchiseptica* (*B. bronchiseptica*) strain that comprises a nucleic acid encoding an antigenic fragment of canine influenza virus H3 hemagglutinin protein; wherein said nucleic acid is operably linked to a promoter; and whereby said live aro mutant *B. bronchiseptica* strain can express the antigenic fragment of canine influenza virus H3 hemagglutinin protein.

22. The immunogenic composition of claim 21, wherein the immunogenic composition further comprises an aromatic supplement.

23. The vaccine of claim 2, wherein the amount of tyrosine is between 4 µg/mL and 0.4 mg/mL, the amount of tryptophan is between 4 µg/mL and 0.4 mg/mL, and the amount of phenylalanine is between 4 µg/mL and 0.4 mg/mL.

\* \* \* \* \*